United States Patent
Watanabe

(10) Patent No.: US 12,029,604 B2
(45) Date of Patent: Jul. 9, 2024

(54) RADIATION DETECTION APPARATUS AND OUTPUT METHOD

(71) Applicant: CANON KABUSHIKI KAISHA, Tokyo (JP)

(72) Inventor: Minoru Watanabe, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 160 days.

(21) Appl. No.: 17/662,898

(22) Filed: May 11, 2022

(65) Prior Publication Data
US 2022/0265238 A1 Aug. 25, 2022

Related U.S. Application Data

(63) Continuation of application No. PCT/JP2020/035719, filed on Sep. 23, 2020.

(30) Foreign Application Priority Data

Nov. 22, 2019 (JP) ................................ 2019-211704

(51) Int. Cl.
*A61B 6/00* (2024.01)
*A61N 5/10* (2006.01)

(52) U.S. Cl.
CPC ............ *A61B 6/542* (2013.01); *A61N 5/1048* (2013.01); *A61N 5/1071* (2013.01)

(58) Field of Classification Search
CPC ..... A61B 6/542; A61N 5/1048; A61N 5/1071
See application file for complete search history.

(56) References Cited

U.S. PATENT DOCUMENTS

| | | | |
|---|---|---|---|
| 4,679,217 A | 7/1987 | Fairchild |
| 7,205,547 B2 | 4/2007 | Ishii |
| 7,205,568 B2 | 4/2007 | Watanabe |
| 7,381,965 B2 | 6/2008 | Ishii |

(Continued)

FOREIGN PATENT DOCUMENTS

| | | |
|---|---|---|
| CN | 101861185 A | 10/2010 |
| CN | 103826538 A | 5/2014 |

(Continued)

OTHER PUBLICATIONS

Chen, Wei et al., Quality Control of a Thermoluminescence Detection System in Entrance Surface Dose Investigation, J. Environ Occup. Med., Sep. 2013, vol. 30, No. 9.

*Primary Examiner* — Blake C Riddick
(74) *Attorney, Agent, or Firm* — VENABLE LLP

(57) ABSTRACT

A radiation detection apparatus capable of monitoring a radiation dose during incidence, includes an obtaining unit configured to obtain a setting of an imaging range including a plurality of parts of an object and a setting of at least one target part that is a target of automatic exposure control in the plurality of parts, a specifying unit configured to specify, based on radiation transmission amounts set for the plurality of parts and radiation doses monitored in a plurality of detection regions of the radiation detection apparatus, at least one target detection region located at a position where radiation transmitted through the at least one target part enters from the plurality of detection regions, and an output unit configured to output the radiation dose monitored in the at least one target detection region.

10 Claims, 10 Drawing Sheets

(56) References Cited

U.S. PATENT DOCUMENTS

| | | | | | |
|---|---|---|---|---|---|
| 7,435,968 B2 | 10/2008 | Watanabe | | | |
| 7,465,933 B2 | 12/2008 | Ishii | | | |
| 7,470,908 B2 | 12/2008 | Ishii | | | |
| 7,488,948 B2 | 2/2009 | Ishii | | | |
| 7,535,506 B2 | 5/2009 | Nomura | | | |
| 7,541,617 B2 | 6/2009 | Mochizuki | | | |
| 7,557,355 B2 | 7/2009 | Mochizuki | | | |
| 7,629,564 B2 | 12/2009 | Mochizuki | | | |
| 7,642,517 B2 | 1/2010 | Ishii | | | |
| 7,645,976 B2 | 1/2010 | Watanabe | | | |
| 7,750,422 B2 | 7/2010 | Watanabe | | | |
| 7,812,313 B2 | 10/2010 | Mochizuki | | | |
| 7,812,317 B2 | 10/2010 | Watanabe | | | |
| 7,858,947 B2 | 12/2010 | Mochizuki | | | |
| 7,897,930 B2 | 3/2011 | Mochizuki | | | |
| 7,923,695 B2 | 4/2011 | Ishii | | | |
| 7,932,946 B2 | 4/2011 | Ishii | | | |
| 8,067,743 B2 | 11/2011 | Ishii | | | |
| 8,084,745 B2 | 12/2011 | Mochizuki | | | |
| 8,154,641 B2 | 4/2012 | Nomura | | | |
| 8,368,027 B2 | 2/2013 | Ishii | | | |
| 8,519,344 B2 | 8/2013 | Ishii | | | |
| 8,680,472 B2 | 3/2014 | Mochizuki | | | |
| 8,878,972 B2 | 11/2014 | Wayama | | | |
| 9,270,903 B2 | 2/2016 | Wayama | | | |
| 9,277,896 B2 | 3/2016 | Ofuji | | | |
| 9,423,513 B2 | 8/2016 | Watanabe | | | |
| 9,521,347 B2 | 12/2016 | Kawanabe | | | |
| 9,625,585 B1 | 4/2017 | Yokoyama | | | |
| 9,661,240 B2 | 5/2017 | Fujiyoshi | | | |
| 9,675,307 B2 | 6/2017 | Ofuji | | | |
| 9,726,767 B2 | 8/2017 | Kawanabe | | | |
| 9,835,732 B2 | 12/2017 | Fujiyoshi | | | |
| 9,838,638 B2 | 12/2017 | Furumoto | | | |
| 9,948,871 B2 | 4/2018 | Wayama | | | |
| 9,977,135 B2 | 5/2018 | Yokoyama | | | |
| 10,068,943 B2 | 9/2018 | Fujiyoshi | | | |
| 10,473,801 B2 | 11/2019 | Kawanabe | | | |
| 10,537,295 B2 | 1/2020 | Watanabe | | | |
| 10,634,800 B2 | 4/2020 | Yokoyama | | | |
| 10,653,372 B2 | 5/2020 | Wayama | | | |
| 10,914,849 B2 | 2/2021 | Ofuji | | | |
| 11,067,706 B2 | 7/2021 | Furumoto | | | |
| 11,083,430 B2 | 8/2021 | Sato | | | |
| 11,090,018 B2 | 8/2021 | Watanabe | | | |
| 11,157,059 B2 | 10/2021 | Yokoyama | | | |
| 11,243,314 B2 | 2/2022 | Fujiyoshi | | | |
| 11,294,078 B2 | 4/2022 | Miura | | | |
| 2004/0156473 A1* | 8/2004 | Nonaka | H05G 1/26 | 378/62 |
| 2005/0169425 A1* | 8/2005 | Takasawa | A61B 6/547 | 378/97 |
| 2008/0080671 A1 | 4/2008 | Nakayama | | |
| 2009/0175528 A1* | 7/2009 | Miyamoto | G06T 7/12 | 382/132 |
| 2010/0008465 A1* | 1/2010 | Matsuura | A61B 6/4085 | 378/92 |
| 2010/0054398 A1* | 3/2010 | Ohta | A61B 6/00 | 378/28 |
| 2011/0044429 A1 | 2/2011 | Takahashi | | |
| 2011/0110497 A1* | 5/2011 | Nishino | A61B 6/4283 | 378/116 |
| 2011/0164724 A1* | 7/2011 | Ohta | A61B 6/06 | 378/97 |
| 2012/0051510 A1* | 3/2012 | Ohta | A61B 6/00 | 378/62 |
| 2012/0051522 A1* | 3/2012 | Nishino | A61B 6/488 | 378/108 |
| 2012/0138811 A1* | 6/2012 | Takenaka | G01T 1/17 | 250/394 |
| 2012/0300904 A1* | 11/2012 | Shimada | A61B 6/463 | 378/62 |
| 2012/0318986 A1* | 12/2012 | Kanagawa | H04N 5/32 | 250/354.1 |
| 2013/0058453 A1* | 3/2013 | Kuwabara | A61B 6/542 | 378/97 |
| 2013/0058454 A1* | 3/2013 | Kuwabara | A61B 6/548 | 378/62 |
| 2013/0058455 A1* | 3/2013 | Kuwabara | A61B 6/545 | 378/97 |
| 2013/0058456 A1* | 3/2013 | Kuwabara | A61B 6/4233 | 378/97 |
| 2013/0058457 A1* | 3/2013 | Kuwabara | A61B 6/548 | 378/97 |
| 2013/0077744 A1 | 3/2013 | Kamiya | | |
| 2013/0121464 A1* | 5/2013 | Tajima | A61B 6/548 | 378/97 |
| 2013/0129053 A1* | 5/2013 | Takahashi | H04N 5/32 | 378/91 |
| 2013/0140465 A1* | 6/2013 | Nishinou | G03B 42/02 | 250/366 |
| 2013/0148782 A1* | 6/2013 | Tajima | A61B 6/545 | 378/62 |
| 2013/0148784 A1* | 6/2013 | Tajima | A61B 6/4283 | 378/62 |
| 2013/0182823 A1* | 7/2013 | Kuwabara | A61B 6/542 | 378/91 |
| 2013/0208852 A1* | 8/2013 | Koishi | A61B 6/5288 | 378/19 |
| 2013/0223592 A1* | 8/2013 | Sato | A61B 6/542 | 378/97 |
| 2013/0251106 A1* | 9/2013 | Tajima | A61B 6/4233 | 378/97 |
| 2013/0279644 A1* | 10/2013 | Yanagida | A61B 6/10 | 378/8 |
| 2013/0342514 A1 | 12/2013 | Yokoyama | | |
| 2014/0023179 A1* | 1/2014 | Oda | H04N 5/32 | 378/91 |
| 2014/0029722 A1* | 1/2014 | Matsumoto | A61B 6/4441 | 378/62 |
| 2014/0056408 A1* | 2/2014 | Tajima | A61B 6/542 | 378/116 |
| 2014/0061488 A1* | 3/2014 | Sato | G01T 1/17 | 250/370.08 |
| 2014/0061492 A1* | 3/2014 | Sato | A61B 6/542 | 250/394 |
| 2014/0061494 A1* | 3/2014 | Sato | H04N 5/32 | 250/394 |
| 2014/0064448 A1* | 3/2014 | Ito | A61B 6/542 | 378/97 |
| 2014/0072103 A1* | 3/2014 | Kitano | A61B 6/4233 | 378/62 |
| 2014/0086391 A1* | 3/2014 | Ohta | H04N 25/53 | 378/91 |
| 2014/0119509 A1* | 5/2014 | Kaneko | A61B 6/4233 | 378/62 |
| 2014/0151769 A1 | 6/2014 | Wayama | | |
| 2014/0154833 A1 | 6/2014 | Wayama | | |
| 2014/0177798 A1* | 6/2014 | Kitagawa | A61B 6/56 | 378/62 |
| 2014/0185764 A1* | 7/2014 | Takenaka | H05G 1/38 | 378/91 |
| 2014/0205066 A1* | 7/2014 | Kitagawa | A61B 6/542 | 378/62 |
| 2014/0211922 A1* | 7/2014 | Kuwabara | A61B 6/56 | 378/97 |
| 2014/0219421 A1* | 8/2014 | Takasawa | A61B 6/461 | 378/62 |
| 2014/0219422 A1* | 8/2014 | Nishino | G01T 1/246 | 378/62 |
| 2014/0239187 A1* | 8/2014 | Iwashita | H04N 5/32 | 250/394 |
| 2014/0341350 A1* | 11/2014 | Muroi | A61B 6/504 | 378/62 |
| 2014/0348300 A1* | 11/2014 | Lee | H04N 5/32 | 378/98.2 |
| 2015/0030129 A1* | 1/2015 | Tajima | A61B 6/4291 | 378/62 |
| 2015/0036802 A1* | 2/2015 | Tajima | A61B 6/4208 | 378/62 |

(56) References Cited

U.S. PATENT DOCUMENTS

| | | | |
|---|---|---|---|
| 2015/0055752 A1* | 2/2015 | Takahashi | H04N 5/32 378/91 |
| 2015/0055753 A1* | 2/2015 | Tajima | A61B 6/4283 378/62 |
| 2015/0078528 A1* | 3/2015 | Okada | G01T 1/15 378/97 |
| 2015/0092911 A1* | 4/2015 | Noji | A61B 6/4035 378/8 |
| 2015/0131784 A1* | 5/2015 | Tajima | G01T 1/1603 378/97 |
| 2015/0153464 A1* | 6/2015 | Imamura | A61B 6/58 378/207 |
| 2015/0164458 A1* | 6/2015 | Tajima | H01L 27/14605 378/97 |
| 2015/0164459 A1* | 6/2015 | Ito | A61B 6/405 378/97 |
| 2015/0182182 A1* | 7/2015 | Tajima | A61B 6/542 378/189 |
| 2015/0189194 A1* | 7/2015 | Tajima | H04N 5/32 378/62 |
| 2015/0192684 A1* | 7/2015 | Ito | G01T 7/005 250/361 R |
| 2015/0245807 A1* | 9/2015 | Tajima | A61B 6/5294 378/98 |
| 2015/0297167 A1* | 10/2015 | Tsuji | H05G 1/56 378/97 |
| 2015/0310597 A1* | 10/2015 | Ohguri | A61B 6/00 382/275 |
| 2015/0331116 A1* | 11/2015 | Matsuura | A61B 6/4216 250/394 |
| 2015/0362601 A1* | 12/2015 | Ofuji | G01N 23/04 250/394 |
| 2015/0363926 A1* | 12/2015 | Enomoto | A61B 6/5205 382/132 |
| 2016/0021290 A1* | 1/2016 | Yagi | H04N 5/33 250/394 |
| 2016/0025865 A1* | 1/2016 | Wayama | A61B 6/542 250/370.07 |
| 2016/0029986 A1* | 2/2016 | Nishii | A61B 6/4233 250/394 |
| 2016/0029993 A1* | 2/2016 | Hiroike | A61B 6/4266 378/91 |
| 2016/0038114 A1* | 2/2016 | Tajima | A61B 6/5294 378/97 |
| 2016/0113615 A1* | 4/2016 | Lee | A61B 6/0487 250/336.1 |
| 2016/0161617 A1* | 6/2016 | Kawanabe | H04N 5/32 250/370.08 |
| 2016/0183908 A1* | 6/2016 | Hayashida | A61B 6/4291 378/207 |
| 2016/0287192 A1 | 10/2016 | Cai | |
| 2016/0345928 A1* | 12/2016 | Jung | A61B 6/542 |
| 2016/0377737 A1* | 12/2016 | Okada | G01T 1/17 250/394 |
| 2017/0027533 A1 | 2/2017 | Sakaguchi | |
| 2017/0090041 A1* | 3/2017 | Yokoyama | H04N 5/32 |
| 2017/0128033 A1* | 5/2017 | Ofuji | A61B 6/4233 |
| 2017/0296133 A1* | 10/2017 | Katsumata | A61B 6/50 |
| 2017/0322484 A1 | 11/2017 | Erhard | |
| 2018/0000442 A1* | 1/2018 | Hiroike | A61B 6/54 |
| 2018/0031715 A1* | 2/2018 | Kuwabara | A61B 6/482 |
| 2018/0055464 A1* | 3/2018 | Watanabe | H01L 27/14663 |
| 2018/0055473 A1* | 3/2018 | Torii | A61B 6/542 |
| 2018/0070906 A1* | 3/2018 | Terui | G06T 11/005 |
| 2018/0095181 A1* | 4/2018 | Kosuge | H04N 5/32 |
| 2018/0108118 A1* | 4/2018 | Takahashi | A61B 6/5235 |
| 2018/0116622 A1* | 5/2018 | Jan | A61B 6/405 |
| 2018/0129120 A1* | 5/2018 | Sato | A61B 6/542 |
| 2018/0136343 A1* | 5/2018 | Terui | H04N 25/76 |
| 2018/0217271 A1* | 8/2018 | Cho | G01T 1/18 |
| 2018/0231672 A1* | 8/2018 | Yokoyama | G01N 23/04 |
| 2018/0263581 A1* | 9/2018 | Cho | G01T 1/24 |
| 2019/0045612 A1 | 2/2019 | Tamura | |
| 2020/0200923 A1* | 6/2020 | Nishihara | A61B 6/44 |
| 2020/0348424 A1 | 11/2020 | Watanabe | |
| 2022/0247911 A1 | 8/2022 | Watanabe | |

FOREIGN PATENT DOCUMENTS

| | | |
|---|---|---|
| CN | 109069089 A | 12/2018 |
| JP | 2001-149359 A | 6/2001 |
| JP | 2011-212424 A | 10/2011 |
| JP | 2013-70723 A | 4/2013 |
| JP | 2016-29987 A | 3/2016 |
| JP | 2017-23695 A | 2/2017 |
| JP | 2017-534401 A | 11/2017 |
| JP | 2017-220403 A | 12/2017 |
| WO | 2016/079047 A1 | 5/2016 |

\* cited by examiner

RADIATION DETECTION APPARATUS AND OUTPUT METHOD

CROSS-REFERENCE TO RELATED APPLICATIONS

This application is a Continuation of International Patent Application No. PCT/JP2020/035719, filed Sep. 23, 2020, which claims the benefit of Japanese Patent Application No. 2019-211704, filed Nov. 22, 2019, both of which are hereby incorporated by reference herein in their entirety.

BACKGROUND OF THE INVENTION

Field of the Invention

The present invention relates to a radiation detection apparatus and an output method.

Description of the Related Art

A radiation detection apparatus for performing automatic exposure control has been put into practical use. Japanese Patent Laid-Open No. 2016-29987 proposes a radiation detection apparatus in which detection pixels configured to monitor a radiation dose during incidence are arranged in a pixel array, and detection signals are read from signal lines connected to the detection pixels. To improve detection accuracy, this radiation detection apparatus discriminates a direct irradiated region or a non-irradiation region and performs automatic exposure using photoelectric conversion elements in a region where radiation has passed through a human body.

To improve image quality in a region of interest, it is considered that automatic exposure control is performed in a detection region located at a position corresponding to the region of interest in the radiation detection apparatus. If a fixed-type radiation detection apparatus is used, it is easy to specify the detection region located at the position corresponding to the region of interest. However, if a portable radiation detection apparatus is used, it may be difficult to specify the detection region. For example, a case in which a lung field part is set as the region of interest, and a chest portion is captured will be examined. At this time, the radiographer installs the radiation detection apparatus such that the lung field part overlaps the upper half of the radiation detection apparatus. However, if the radiographer installs the radiation detection apparatus rotated 180° by mistake, the upper half of the radiation detection apparatus overlaps the abdominal part. For this reason, a radiation dose transmitted through the abdominal part overlapping the upper half of the radiation detection apparatus is monitored, and automatic exposure control cannot correctly be performed. One aspect of the present disclosure provides a technique for accurately specifying a detection region as a target of automatic exposure control.

SUMMARY OF THE INVENTION

In an embodiment, a radiation detection apparatus capable of monitoring a radiation dose during incidence, includes an obtaining unit configured to obtain a setting of an imaging range including a plurality of parts of an object and a setting of at least one target part that is a target of automatic exposure control in the plurality of parts, a specifying unit configured to specify, based on radiation transmission amounts set for the plurality of parts and radiation doses monitored in a plurality of detection regions of the radiation detection apparatus, at least one target detection region located at a position where radiation transmitted through the at least one target part enters from the plurality of detection regions, and an output unit configured to output the radiation dose monitored in the at least one target detection region.

Further features of the present invention will become apparent from the following description of exemplary embodiments with reference to the attached drawings.

DESCRIPTION OF THE EMBODIMENTS

Figure 1:
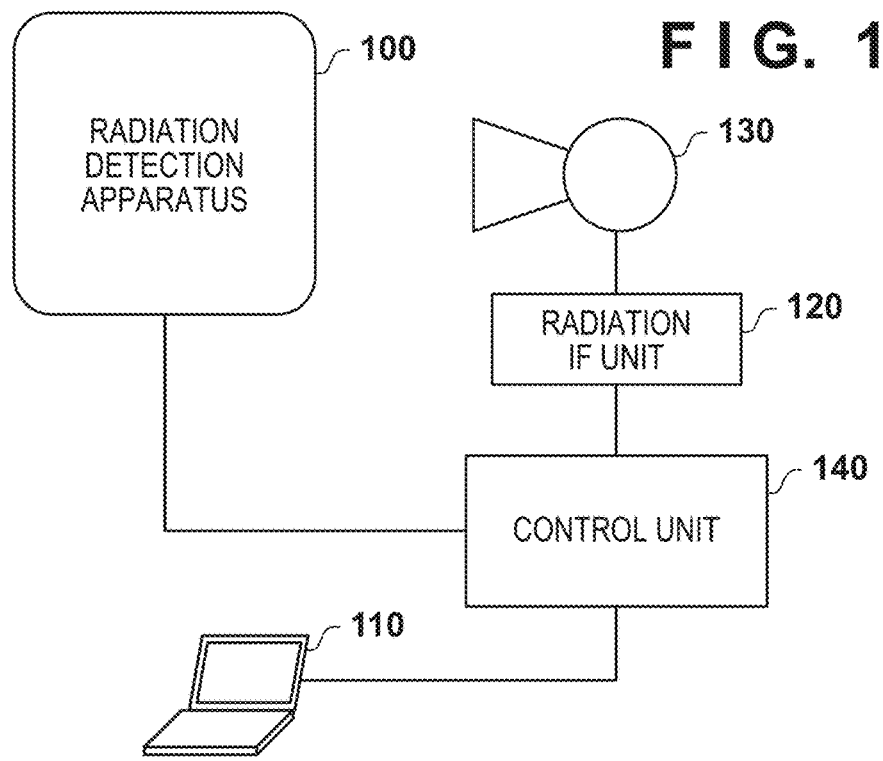
FIG. 1 is a view for explaining an example of the configuration of a radiation detection system according to the embodiment of the present disclosure.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

An example of the configuration of a radiation detection system according to some embodiments will be described with reference to FIG. 1. The configuration of the radiation detection system may be the same as an existing configuration, and an example will be described below. In this specification, radiation may include not only α-rays, β-rays, γ-rays, and the like, which are beams generated by particles (including photons) emitted by radioactive decay but also beams having equal or more energy, for example, X-rays, particle beams, and cosmic rays. The radiation detection system shown in FIG. 1 may include a radiation detection apparatus 100, a control console 110, a radiation interface unit 120, and a radiation source 130. The radiation detection apparatus 100, the control console 110, and the radiation interface unit 120 are connected by a control unit 140 to be communicable with each other. The control unit 140 and each device may be connected by wire or wirelessly. In the communication between the devices, a communication delay according to the communication method or communication contents occurs. The radiation detection system may manage the value of the communication delay.

The control console 110 is a device used by the user (for example, a doctor or a radiographic technician and will be simply referred to as a user hereinafter) of the radiation detection system to operate the radiation detection system. The radiation source 130 is a device that generates radiation. The radiation source 130 starts and stops radiation irradiation in accordance with an instruction from the radiation interface unit 120. The radiation detection apparatus 100 is an apparatus configured to detect radiation that has entered itself. The radiation detection apparatus 100 may be used as a medical image diagnosis apparatus, a non-destructive inspection apparatus, or an analysis apparatus using radiation. The radiation detection apparatus 100 can monitor a radiation dose that has entered itself. Based on the radiation dose monitored by the radiation detection apparatus 100, the radiation detection system performs automatic exposure control (to be referred to as AEC (Auto Exposure Control) hereinafter) by the control unit 140. The radiation detection apparatus 100 has an effective region of, for example, 17 inch (431.8 mm) square.

The operation of the radiation detection system will briefly be described below. This operation may be the same as the operation of an existing radiation detection system. The control console 110 obtains imaging settings from the user before the start of imaging. The imaging settings may include, for example, the type of an object, the imaging range of the object, a region of interest (ROI) in the imaging range, and the like. In accordance with the imaging settings, the control console 110 decides imaging conditions such as the irradiation upper limit time of the radiation source 130, a tube current, and a tube voltage.

When an exposure switch is pressed after the decision of the imaging conditions, the radiation source 130 starts radiation irradiation to the radiation detection apparatus 100. The radiation emitted from the radiation source 130 passes through an object placed between the radiation detection apparatus 100 and the radiation source 130 and enters the radiation detection apparatus 100. The radiation detection apparatus 100 monitors the radiation dose during incidence. If the radiation dose under monitoring reaches a threshold, the radiation detection apparatus 100 generates radiation dose monitor information necessary for stopping the radiation irradiation of the radiation source 130. Upon determining, based on the monitor information, that the radiation dose under monitoring reaches the threshold, the control unit 140 generates a signal (to be referred to as an exposure stop signal hereinafter) for stopping the radiation irradiation of the radiation source 130. The radiation source 130 that has received the exposure stop signal stops the radiation irradiation. The radiation source 130 stops the radiation irradiation even if the irradiation upper limit time is reached before reception of the exposure stop signal. After the radiation irradiation is stopped, the radiation detection apparatus 100 measures the radiation dose of radiation that has entered itself, and transmits a radiation image based on the value to the control console 110. The control console 110 may display the radiation image to the user or store the radiation image in a storage unit. The radiation detection apparatus 100 may only generate radiation dose information under monitoring and output it to the control unit 140 that controls radiation irradiation, or may output a control signal to stop radiation irradiation. In the following embodiment, the former case, that is, a form in which the radiation detection apparatus 100 generates radiation dose information under monitoring and outputs the radiation dose information to the control unit 140 that controls radiation irradiation will mainly be described.

Figure 2:
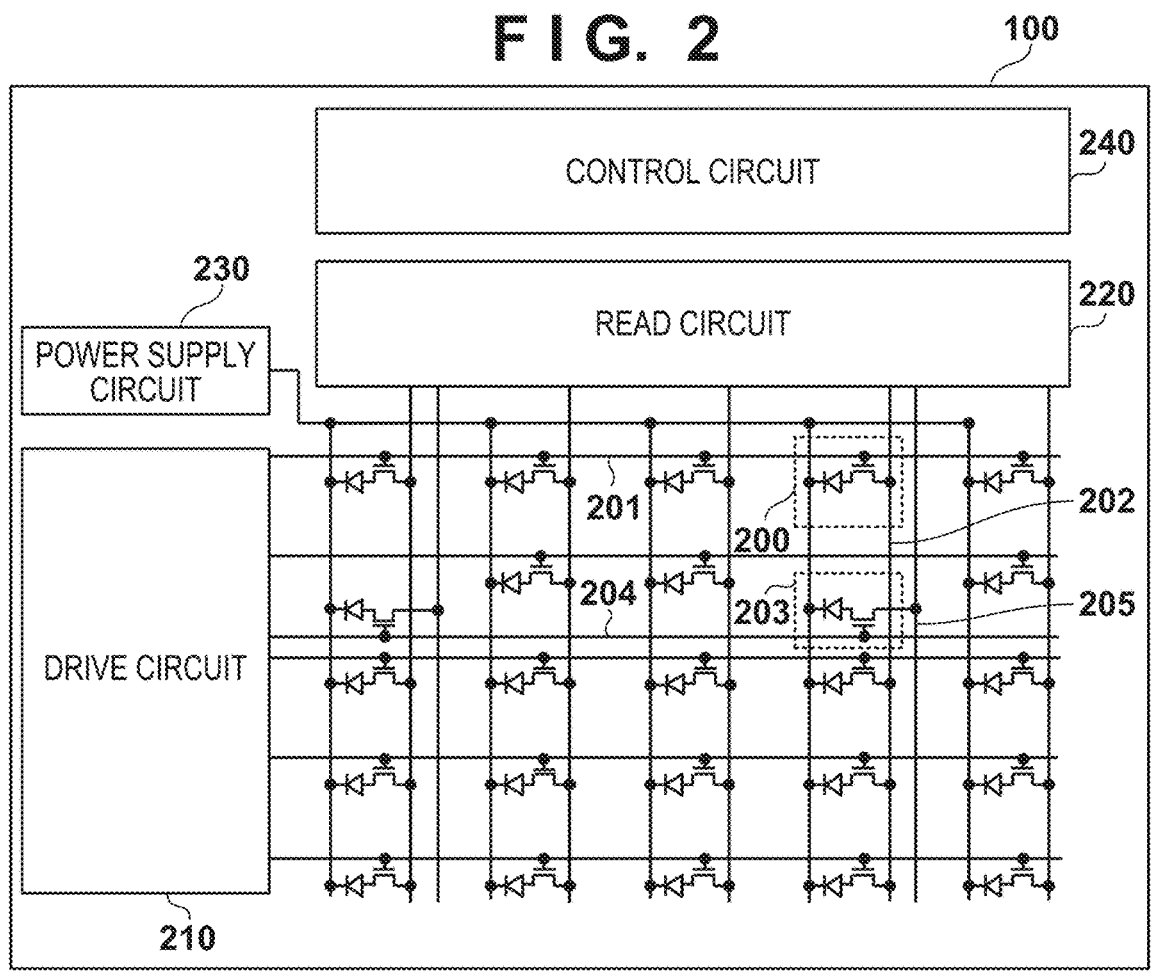
FIG. 2 is a view for explaining an example of the configuration of a radiation detection apparatus according to the embodiment of the present disclosure.

An example of the configuration of the radiation detection apparatus 100 will be described with reference to FIG. 2. FIG. 2 shows an example of the configuration of the radiation detection apparatus 100 capable of monitoring the radiation dose during incidence, and another configuration may be employed. The radiation detection apparatus 100 includes a plurality of pixels, a drive circuit 210, a read circuit 220, a power supply circuit 230, and a control circuit 240.

The plurality of pixels are arranged in a matrix to form a pixel array. In the example shown in FIG. 2, the pixels are arranged in 5 rows×5 columns. However, the size of the pixel array is not limited to this. Each pixel generates a signal according to an incident radiation dose. The drive circuit 210 scans a plurality of drive lines 201 and 204, thereby allowing the read circuit 220 to read out charges accumulated in the pixels. The read circuit 220 reads out signals from the pixels via a plurality of signal lines 202 and 205. The read circuit 220 may perform amplification or analog/digital conversion of readout signals. The power supply circuit 230 supplies a bias voltage to the photoelectric conversion element of each pixel. The control circuit 240 controls the operation of the entire radiation detection apparatus 100. Here, the control circuit 240 may function as a control device of the radiation detection apparatus 100. More specifically, the control circuit 240 may supply control signals to the drive circuit 210 and the read circuit 220, thereby controlling the operations of these. Also, the control circuit 240 may communicate with an apparatus outside the radiation detection apparatus 100. For example, the control circuit 240 may receive an instruction from the control console 110, transmit an instruction to the radiation source 130, or transmit a radiation image to the control console 110.

The plurality of pixels include a plurality of image pixels 200 and a plurality of monitor pixels 203. The image pixel 200 is a pixel configured to generate a radiation image. The monitor pixel 203 is a pixel configured to monitor a radiation dose during incidence. During incidence of radiation, the drive circuit 210 periodically supplies an ON signal (a signal for turning on a switch element in a pixel) to the drive line 204. Accordingly, a signal accumulated in each monitor pixel 203 is read out to the read circuit 220 via the signal line 205. The control circuit 240 integrates the radiation doses read out from the monitor pixels 203 and outputs the radiation dose. Also, the control circuit 240 may integrate the radiation doses read out from the monitor pixels 203, determine whether the integrated radiation dose reaches a threshold, and output a control signal based on the determination result. During radiation irradiation, the drive circuit 210 continuously supplies an OFF signal (a signal for turning off a switch element in a pixel) to the drive line 201. Hence, charges are continuously accumulated in each image pixel 200 during monitoring of the radiation dose. After the radiation irradiation stops, the drive circuit 210 supplies the ON signal to the drive line 201. Accordingly, a signal accumulated in each image pixel 200 is read out to the read circuit 220 via the signal line 202. The control circuit 240 generates a radiation image as well based on the signal.

The plurality of monitor pixels 203 are dispersedly in the region of the pixel array. For example, if the pixel array is equally divided into 3×3=9 sections, the plurality of monitor pixels 203 may be dispersed such that each section includes a monitor pixel. Alternatively, the plurality of monitor pixels 203 may be dispersed such that a monitor pixel 203 is included in each of sections formed by more finely equally dividing the pixel array.

Figure 3A:
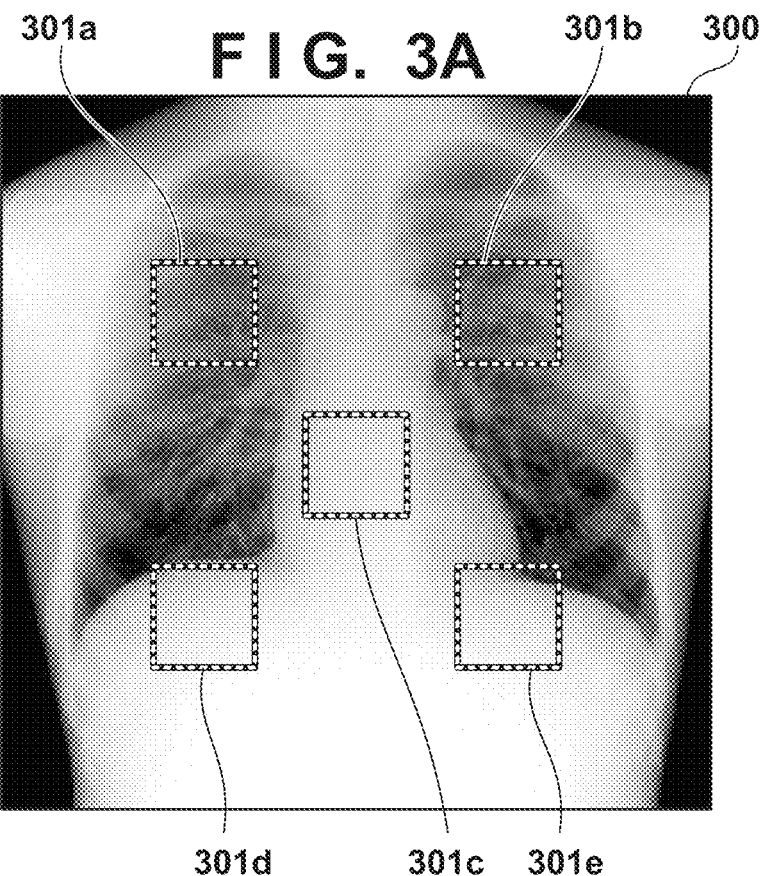
FIG. 3A is a view for explaining an example of an imaging range and detection regions according to the embodiment of the present disclosure.
Figure 3B:
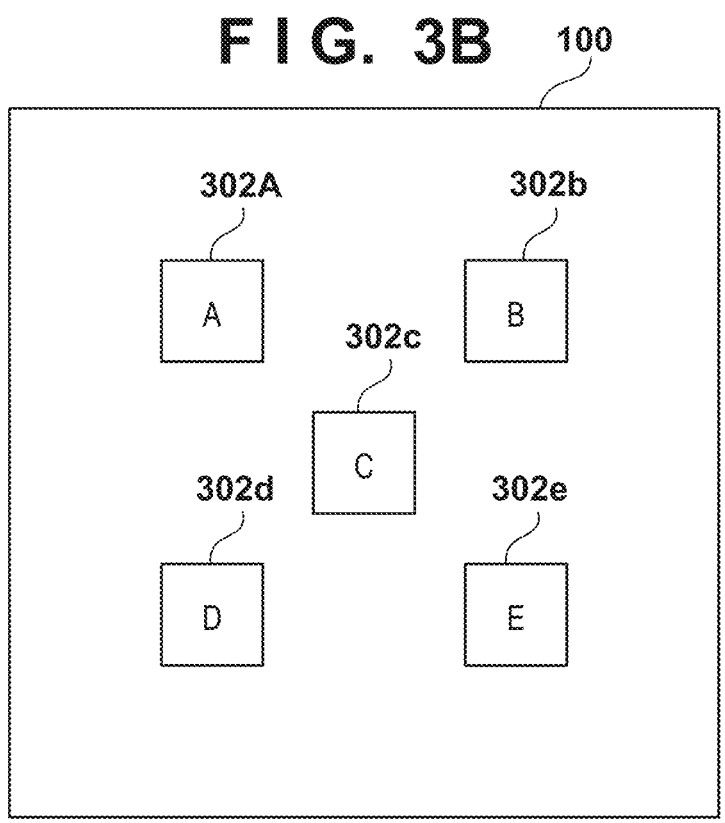
FIG. 3B is a view for explaining an example of an imaging range and detection regions according to the embodiment of the present disclosure.

Detection regions of the radiation detection apparatus 100 will be described with reference to FIGS. 3A and 3B. A detection region is a region where the radiation dose during incidence is monitored in the radiation detection apparatus 100. FIG. 3A shows an imaging range 300 of an object to be captured using the radiation detection apparatus 100. FIG. 3B shows a plurality of detection regions 302a to 302e set for the imaging range 300 in the radiation detection apparatus 100. In the example shown in FIG. 3A, the imaging range 300 is the front chest portion of a human body. The imaging range is not limited to this, and may be another portion of the human body, or a portion of an object other than a human body.

The imaging range 300 includes a plurality of parts of the object. If the imaging range 300 is the front chest portion, as shown in FIG. 3A, the imaging range 300 includes lung field parts 301a and 301b, a mediastinal part 301c, and abdominal parts 301d and 301e. The user sets at least one part of the plurality of parts included in the imaging range 300 to the target of AEC. The part set as the target of AEC is called a target part. The target part may be one part or include a plurality of parts. The target part may be the same as the region of interest or different. For example, assume that the user sets the lung field parts 301a and 301b of the plurality of parts included in the imaging range 300 to the region of interest. In this case, the control circuit 240 may set the lung field parts 301a and 301b to the target part. Also, the user may set the mediastinal part 301c to the target part while setting the lung field parts 301a and 301b to the region of interest.

If the radiation detection apparatus 100 is arranged in a correct direction to the object (in the example shown in FIGS. 3A and 3B, the direction in which the upper side of the radiation detection apparatus 100 is located on the head side of the object), radiation transmitted through the lung field parts 301a and 301b enters the detection regions 302a and 302b shown in FIG. 3B. For this reason, the control unit 140 executes AEC by setting the detection regions 302a and 302b to the detection region. However, if the radiation detection apparatus 100 is arranged in a wrong direction to the object, the control unit 140 cannot execute AEC by setting the detection regions 302a and 302b to the detection region. This will be described in detail with reference to FIGS. 4A and 4B.

Figure 4A:
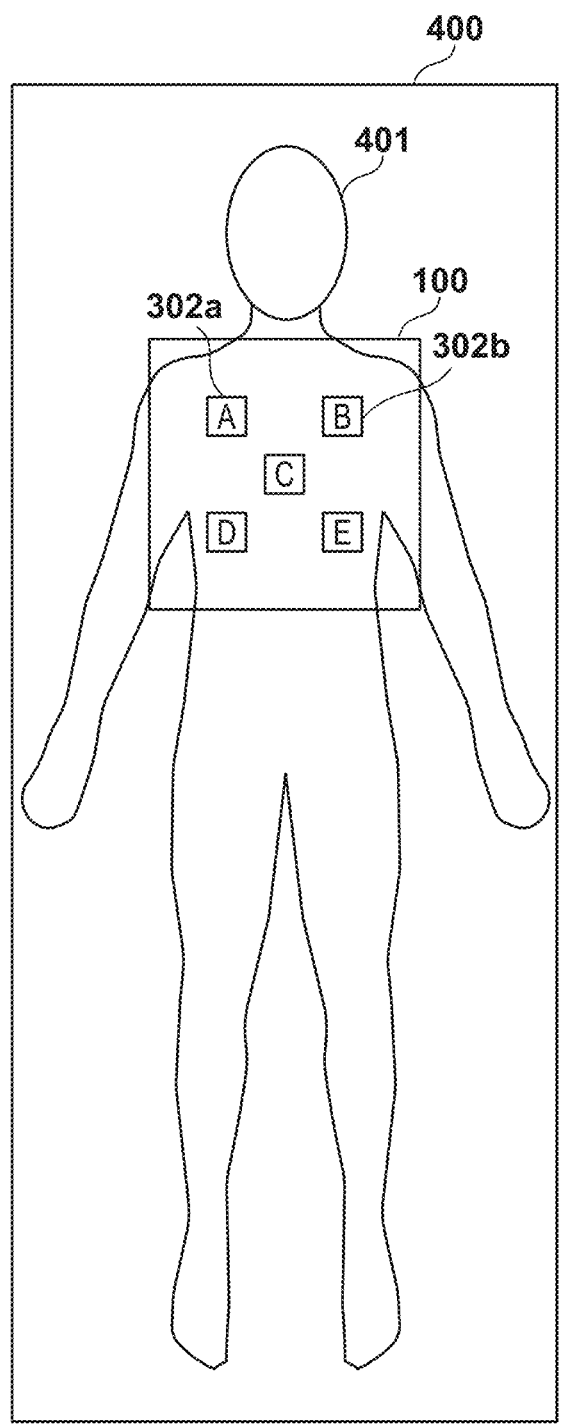
FIG. 4A is a view for explaining an example of the installation position of the radiation detection apparatus according to the embodiment of the present disclosure.
Figure 4B:
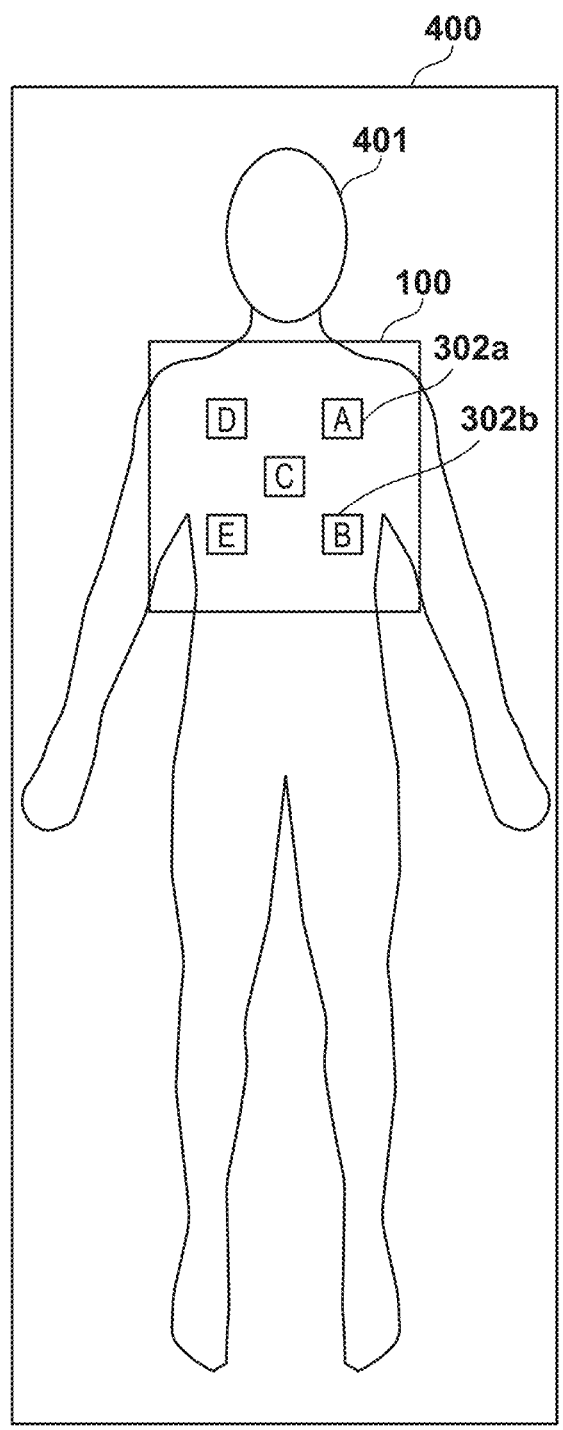
FIG. 4B is a view for explaining an example of the installation position of the radiation detection apparatus according to the embodiment of the present disclosure.

FIGS. 4A and 4B explain the installation direction of the radiation detection apparatus 100 with respect to an object 401. In FIGS. 4A and 4B, the radiation detection apparatus 100 is arranged on a bed 400, and the object 401 lies on his/her back on it. In this state, imaging of the object 401 is performed. In FIG. 4A, the radiation detection apparatus 100 is arranged in the correct direction to the object (the direction in which the upper side of the radiation detection apparatus 100 is located on the head side of the object 401). On the other hand, in FIG. 4B, the radiation detection apparatus 100 is arranged in a wrong direction to the object. More specifically, in FIG. 4B, the radiation detection apparatus 100 is arranged in a direction rotated by 90° clockwise from the correct installation direction. The rotation direction will be defined as clockwise below unless otherwise specified.

If the radiation detection apparatus 100 is correctly arranged, as shown in FIG. 4A, the radiation dose transmitted through the lung field parts 301a and 301b can be monitored by monitoring the radiation dose in the detection regions 302a and 302b of the radiation detection apparatus 100. However, in a case in which the radiation detection apparatus 100 is arranged wrongly, as shown in FIG. 4B, when the radiation dose in the detection regions 302a and 302b of the radiation detection apparatus 100 is monitored, the radiation dose transmitted through the lung field part 301b and the abdominal part 301e is monitored. Since the radiation transmission amount changes between the lung field part and the abdominal part, the control circuit 240 cannot output an appropriate transmission amount for AEC even when the detection region 302b is monitored by setting the lung field part to the target of AEC. The situation in which the radiation detection apparatus 100 is not installed in the correct direction, and AEC cannot be executed occurs not only in imaging on a bed as shown in FIGS. 4A and 4B but also in imaging at a round visit in which a doctor visits beds in ward to obtain radiation images.

Considering the possibility that the installation direction of the radiation detection apparatus 100 is not correct, before execution of AEC, the control circuit 240 of the radiation detection apparatus 100 according to some embodiments specifies at least one region at a position where the radiation transmitted through at least one target part enters. The control circuit 240 outputs the radiation dose to irradiate the target parts, including the specified information, to the control unit 140, and the control unit 140 performs AEC for the at least one region.

A detailed example of the operation of the control circuit 240 will be described with reference to FIGS. 3A and 3B again. The control circuit 240 sets the detection regions 302a and 302b where the radiation transmitted through the lung field parts 301a and 301b enters if the radiation detection apparatus 100 is correctly installed to the detection regions. In addition, the control circuit 240 also sets, as the detection regions, the detection regions 302d and 302e where the radiation transmitted through the lung field parts 301a and 301b enters in the directions in which the radiation detection apparatus 100 is rotated by 90°, 180°, and 270° from the correct installation direction. In some embodiments, the control circuit 240 also sets the detection region 302c at the center of the radiation detection apparatus 100 to the detection region.

Figure 5A:
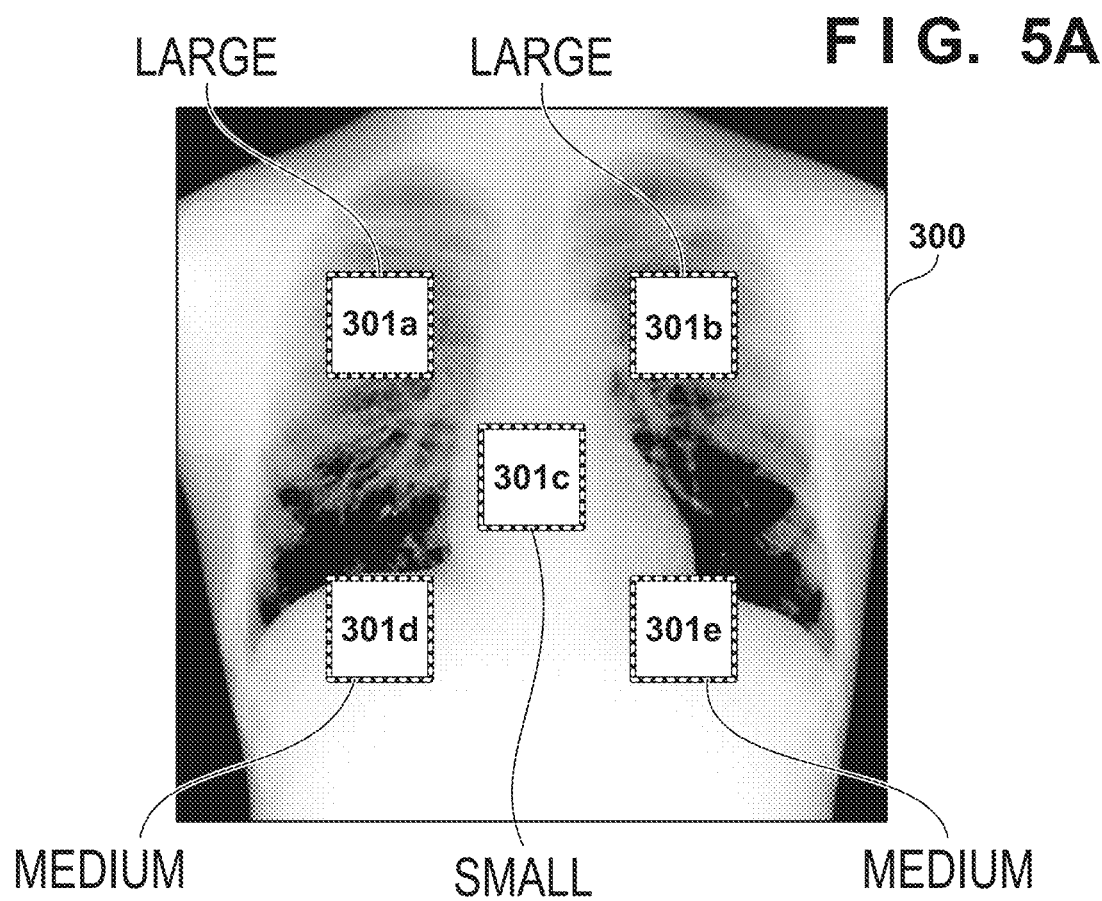
FIG. 5A is a view for explaining an example of the distribution of radiation doses according to the embodiment of the present disclosure.

The control circuit 240 also obtains a distribution of radiation transmission amounts assumed in the plurality of parts (301a to 301e) corresponding to the plurality of detection regions (302a to 302e) determined in this way. Such a radiation transmission amount distribution is set in advance for each imaging range and stored in advance in the storage unit of the radiation detection system (for example, the storage unit of the control console 110 or the storage unit of the control circuit 240). For example, if the front chest portion is the imaging range, like the imaging range 300, the distribution of transmission amounts of the parts is set as shown in FIG. 5A. More specifically, in each of the lung field parts 301a and 301b, many air layers exist, and the absorption amount of irradiated radiation is small. Hence, the radiation transmission amount is large ("large" in FIG. 5A). In each of the abdominal parts 301d and 301e, there are few air layers, and bones are absent. Hence, the radiation transmission amount is medium ("medium" in FIG. 5A). In the mediastinal part 301c, there are few air layers, and bones exist. Hence, the radiation transmission amount is small ("small" in FIG. 5A). The transmission amount in each part may be set as an absolute amount or a relative amount. In the example shown in FIG. 5A, the transmission amounts are set by relative evaluation in three levels "large", "medium", and "small".

Figure 5B:
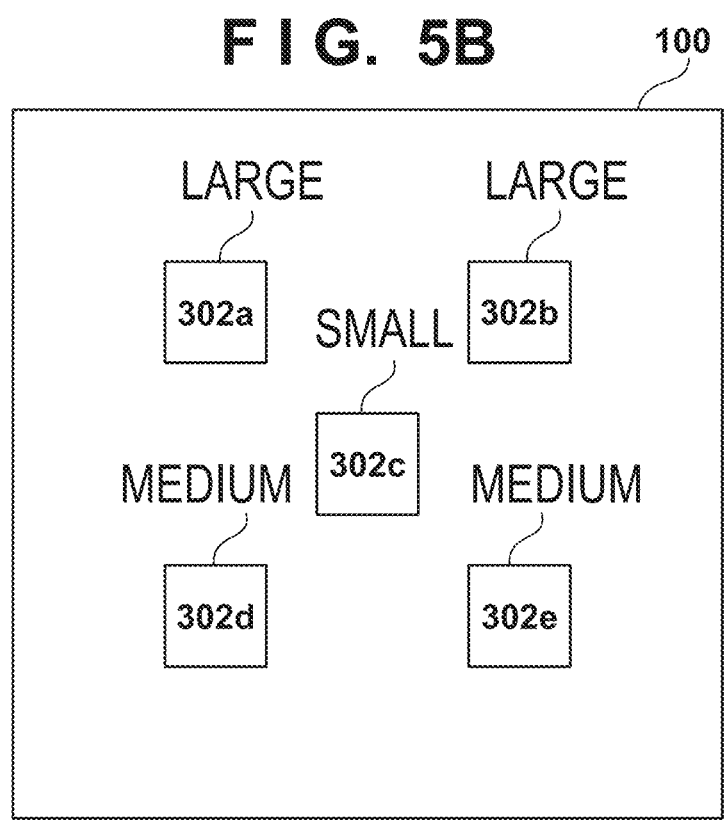
FIG. 5B is a view for explaining an example of the distribution of radiation doses according to the embodiment of the present disclosure.
Figure 5C:
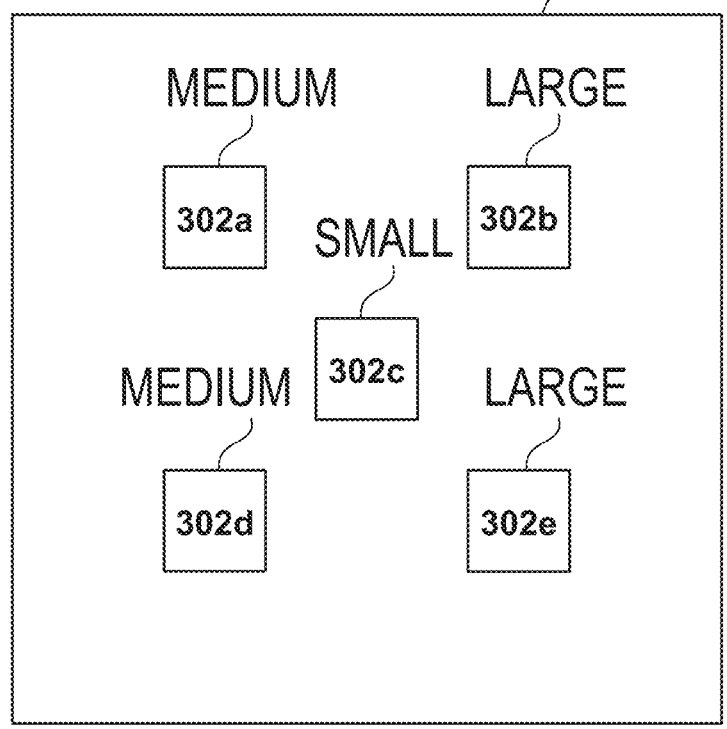
FIG. 5C is a view for explaining an example of the distribution of radiation doses according to the embodiment of the present disclosure.
Figure 5D:
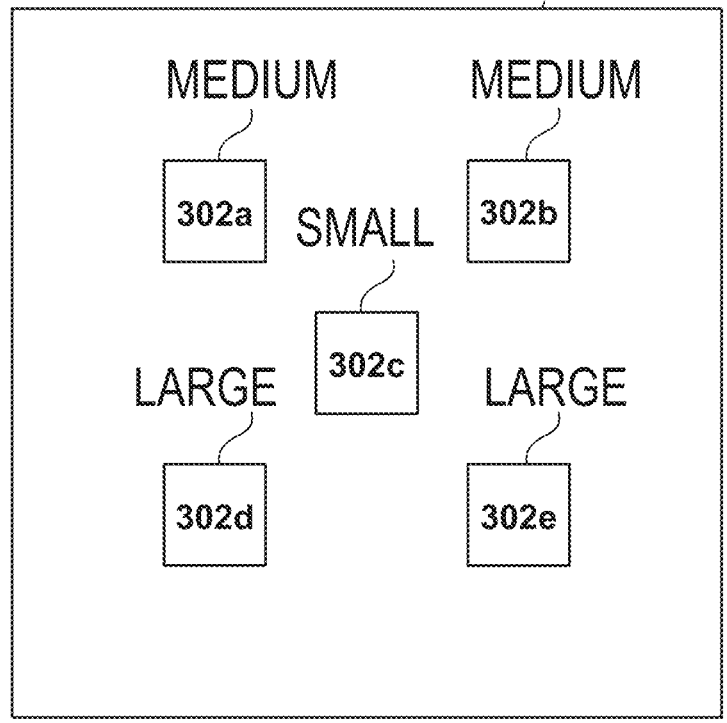
FIG. 5D is a view for explaining an example of the distribution of radiation doses according to the embodiment of the present disclosure.

The control circuit 240 obtains the radiation doses monitored in the plurality of detection regions (the detection regions 302a to 302e) during incidence of radiation. The control circuit 240 compares the distribution of the radiation transmission amounts set for the plurality of parts with the distribution of the radiation doses monitored in the plurality of detection regions, thereby specifying at least one detection region (to be referred to as a target detection region hereinafter) to be set to the target of AEC. The monitored radiation dose may be obtained as an absolute amount or a relative amount. In the examples shown in FIGS. 5B to 5D, the radiation doses are obtained by relative evaluation in three levels "large", "medium", and "small". For example, if the monitored radiation doses are distributed as shown in FIG. 5B, the control circuit 240 determines that the radiation detection apparatus 100 is installed in the correct direction to the object. In this case, the control circuit 240 outputs the radiation doses monitored in the detection regions 302a and 302b. If the monitored radiation doses are distributed as shown in FIG. 5C, the control circuit 240 determines that the radiation detection apparatus 100 is installed in a direction rotated by 90° from the correct direction to the object. In this case, the control circuit 240 outputs the radiation doses monitored in the detection regions 302b and 302e. If the monitored radiation doses are distributed as shown in FIG. 5D, the control circuit 240 determines that the radiation detection apparatus 100 is installed in a direction rotated by 180° from the correct direction to the object. In this case, the control circuit 240 outputs the radiation doses monitored in the detection regions 302d and 302e. Although not illustrated, the control circuit 240 can also determine that the radiation detection apparatus 100 is installed in a direction rotated by 270° from the correct direction to the object.

According to the above-described method, a target detection region corresponding to a target part is specified, and it is determined, based on the radiation dose in the target detection region, whether to step radiation irradiation. Hence, even if the installation direction of the radiation detection apparatus 100 is wrong, AEC can accurately be performed. Since the labor to reinstall the radiation detection apparatus 100 can be saved as a result, burden of the user and the patient decreases.

An example of the operation of the radiation detection apparatus 100 and the control unit 140 will be described with reference to FIGS. 6A and 6B. The steps of the following operation be performed by the general-purpose processor of the control circuit 240 of the radiation detection apparatus 100 or the general-purpose processor of the control unit 140 executing a program stored in the memory of each apparatus. Instead, at least some steps of the following operations may be executed by the dedicated circuit (for example, an ASIC (Application Specific Integrated Circuit)) of the control circuit 240 or the dedicated circuit of the control unit 140.

In step S601, the control circuit 240 obtains the setting of the imaging range and the setting of the target part. The imaging range may be a part of an object or the whole object. The imaging range includes a plurality of parts of the object, as described above. At least one target part as the target of AEC is set from the plurality of parts included in the imaging range. These settings may be obtained from the user via the control console 110. Alternatively, the settings may be obtained from a storage unit that stores conditions set in advance.

In step S602, the control circuit 240 decides the position of a detection region. As described above, the control circuit 240 decides, as the detection region, a region where radiation transmitted through at least one target part enters if the radiation detection apparatus 100 is correctly arranged. Also, the control circuit 240 may also decide, as a detection region, a region located at a position obtained by rotating the at least one detection region decided in the above-described way by 180° with respect to the center of the radiation detection apparatus 100 (or the center of the effective region). As a result, the plurality of detection regions are arranged in two-fold symmetry. Two-fold symmetry is an arrangement in which the arrangement after 180° rotation is the same as the original arrangement. In this case, AEC can correctly be performed even if the radiation detection apparatus 100 is installed while being rotated by 180° from the correct direction.

Furthermore, the control circuit 240 may also decide, as detection regions, regions located at positions obtained by rotating the plurality of detection regions decided in the above-described way by 90° and 270° with respect to the center of the radiation detection apparatus 100 (or the center of the effective region). As a result, the plurality of detection regions are arranged in four-fold symmetry. Four-fold symmetry is an arrangement in which the arrangement after 90° rotation is the same as the original arrangement. In this case, AEC can correctly be performed even if the radiation detection apparatus 100 is installed while being rotated by 90° or 270° from the correct direction. Furthermore, the control circuit 240 may decide, as a detection region, the region at the center of the radiation detection apparatus 100.

In step S603, when the radiation source 130 starts radiation irradiation to the radiation detection apparatus 100 in accordance with an instruction from the user, the control circuit 240 starts monitoring the radiation dose in each of the plurality of detection regions located at the decided positions. The radiation dose monitored in a detection region may be the representative value of signals obtained by one or more monitor pixels 203 included in the detection region. The representative value may be the average value of the signals obtained by the plurality of monitor pixels 203, or may be a median. Also, the radiation dose monitored in the detection region may be decided in consideration of signals obtained by one or more monitor pixels 203 located near the detection region.

In step S604, the control circuit 240 determines whether the radiation dose under monitoring exceeds a threshold. If the radiation dose exceeds the threshold ("YES" in step S604), the control circuit 240 advances the process to step S605. Otherwise ("NO" in step S604), the control circuit 240 repeats step S604.

Figure 7:
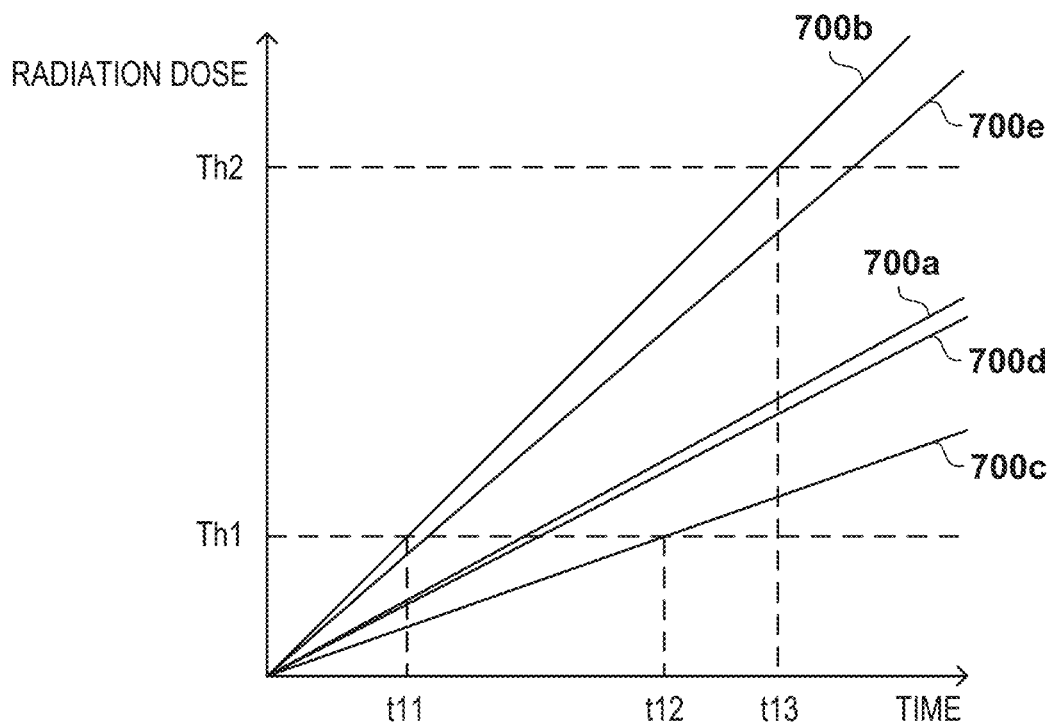
FIG. 7 is a view for explaining an example of radiation dose determination according to the embodiment of the present disclosure.

The method of comparing the radiation dose under monitoring with the threshold will be described with reference to FIG. 7. The abscissa of FIG. 7 represents the time elapsed from the start of radiation dose monitoring, and the ordinate represents the integrated value of radiation doses. Graphs 700*a* to 700*e* correspond to radiation doses monitored in the detection regions 302*a* to 302*e* in FIG. 3B, respectively.

In some embodiments, if the radiation dose in at least one of the plurality of detection regions 302*a* to 302*e* exceeds the threshold, the control circuit 240 determines that the condition of step S604 is satisfied, and advances to subsequent processing. For example, as indicated by the graph 700*b* in FIG. 7, the radiation dose monitored in the detection region 302*b* reaches a threshold Th1 at time t11. Then, the control circuit 240 determines that the condition of step S604 is satisfied at time t11.

In another embodiment, if the radiation doses in all of the plurality of detection regions 302*a* to 302*e* exceed the threshold, the control circuit 240 determines that the condition of step S604 is satisfied, and advances to subsequent processing. For example, as indicated by the graph 700*c* in FIG. 7, the radiation dose monitored in the detection region 302*c* is the last that reaches the threshold Th1 at time t12 in all detection regions. Then, the control circuit 240 determines that the condition of step S604 is satisfied at time t12. In still another embodiment, if the radiation doses in some but not all of the plurality of detection regions 302*a* to 302*e* exceed the threshold, the control circuit 240 may determine that the condition of step S604 is satisfied.

In step S605, based on the radiation transmission amounts set for the plurality of parts and the radiation doses monitored in the plurality of detection regions, the control circuit 240 specifies, from the plurality of detection regions, at least one detection region at a position where the radiation transmitted through at least one target part enters. The detection region specified in this way is called a target detection region.

As described concerning FIG. 3A described above, a radiation transmission amount is set in advance for each of the plurality of parts (301*a* to 301*e*) in the imaging range 300. The control circuit 240 obtains the setting from the storage unit that stores the setting. The control circuit 240 compares the radiation transmission amounts set for the plurality of parts (301*a* to 301*e*) with the radiation doses monitored in the plurality of detection regions 302*a* to 302*e*. For example, the control circuit 240 specifies, as target detection regions, the detection regions of radiation doses corresponding to the radiation transmission amount ("large" in the example shown in FIG. 5A) set for the target parts (the lung field parts 301*a* and 301*b*). In the example shown in FIG. 7, since the radiation doses monitored in the detection regions 302*b* and 302*e* are "large", the control circuit 240 specifies the detection regions 302*b* and 302*e* as the target detection regions.

In some embodiments, the control circuit 240 compares the distribution of the radiation transmission amounts set for the plurality of parts and the distribution of the radiation doses monitored in the plurality of detection regions, thereby specifying at least one target detection region. More specifically, in the example shown in FIG. 7, the radiation doses monitored in the plurality of detection regions 302*a* to 302*e* have the distribution shown in FIG. 5C. When the distribution of the radiation transmission amounts shown in FIG. 5A is rotated by 90°, the distribution matches the distribution of the radiation doses in FIG. 5C. For this reason, the control circuit 240 specifies, as the target detection regions, the detection regions 302*b* and 302*e* located at positions obtained by rotating the lung field parts 301*a* and 301*b* that are the target parts by 90°.

In step S606, the control circuit 240 determines whether a target detection region can be specified. A detection region corresponding to a target part is called a target detection region. If a target detection region can be specified ("YES" in step S606), the control circuit 240 advances the process to step S607. Otherwise ("NO" in step S606), the control circuit 240 advances the process to step S608. For example, if a detection region having the radiation dose corresponding to the radiation transmission amount ("large" in the example shown in FIG. 5A) set for the target part (the lung field parts 301*a* and 301*b*) does not exist, the control circuit 240 determines that a target detection region cannot be specified. In another example, if the distribution of the radiation doses monitored in the detection regions 302*a* to 302*e* in a rotated state does not overlap the distribution of the radiation transmission amounts of the parts (301*a* to 301*e*), the control circuit 240 determines that a target detection region cannot be specified.

In step S607, the control unit 140 determines whether the radiation dose in the target detection region exceeds a threshold. If the radiation dose exceeds the threshold ("YES" in step S607), the control unit 140 advances the process to step S610. Otherwise ("NO" in step S607), the control unit 140 repeats step S607. This step is executed when at least one target detection region can be specified. Hence, the control circuit 240 specifies the at least one target detection region and outputs radiation dose information. Using the output information, the control unit 140 determines whether to stop radiation irradiation. For example, without considering the radiation doses in the remaining detection regions, the control unit 140 may determine whether to stop radiation irradiation based on only one or more target detection regions.

In the example shown in FIG. 7, the control unit 140 may determine whether the radiation dose of one of the two target detection regions (the detection regions 302*b* and 302*e*) exceeds a threshold Th2 at time t13. Instead, the control unit 140 may determine whether all radiation doses in the plurality of target detection regions exceed the threshold Th2, or may determine whether the representative value (for example, the average value or the median) of the radiation doses in the plurality of target detection regions exceeds the threshold Th2.

In step S608, the control circuit 240 notifies the user that a target detection region cannot be specified. Upon receiving the notification, the user may stop imaging of the object.

In step S609, the control unit 140 determines whether the radiation dose in one or more of the detection regions exceeds a threshold. If the radiation dose exceeds the threshold ("YES" in step S609), the control unit 140 advances the process to step S610. Otherwise ("NO" in step S609), the control unit 140 repeats step S609. This step is executed when at least one target detection region can be specified. Hence, based on the radiation dose monitored in one or more of the plurality of detection regions 302*a* to 302*e*, the control unit 140 determines whether to stop radiation irradiation. For example, the control unit 140 may compare the maximum value of the radiation doses in the plurality of detection regions 302*a* to 302*e* with a threshold, compare the minimum value with a threshold, or compare the representative value with a threshold.

In step S610, the control unit 140 generates a signal for instructing stop of radiation irradiation and transmits it to the radiation source 130. Upon receiving the signal, the radiation source 130 stops radiation irradiation. In step S611, the control circuit 240 reads out signals from the image pixels 200 and generates a radiation image based on the signals.

Figure 6A:
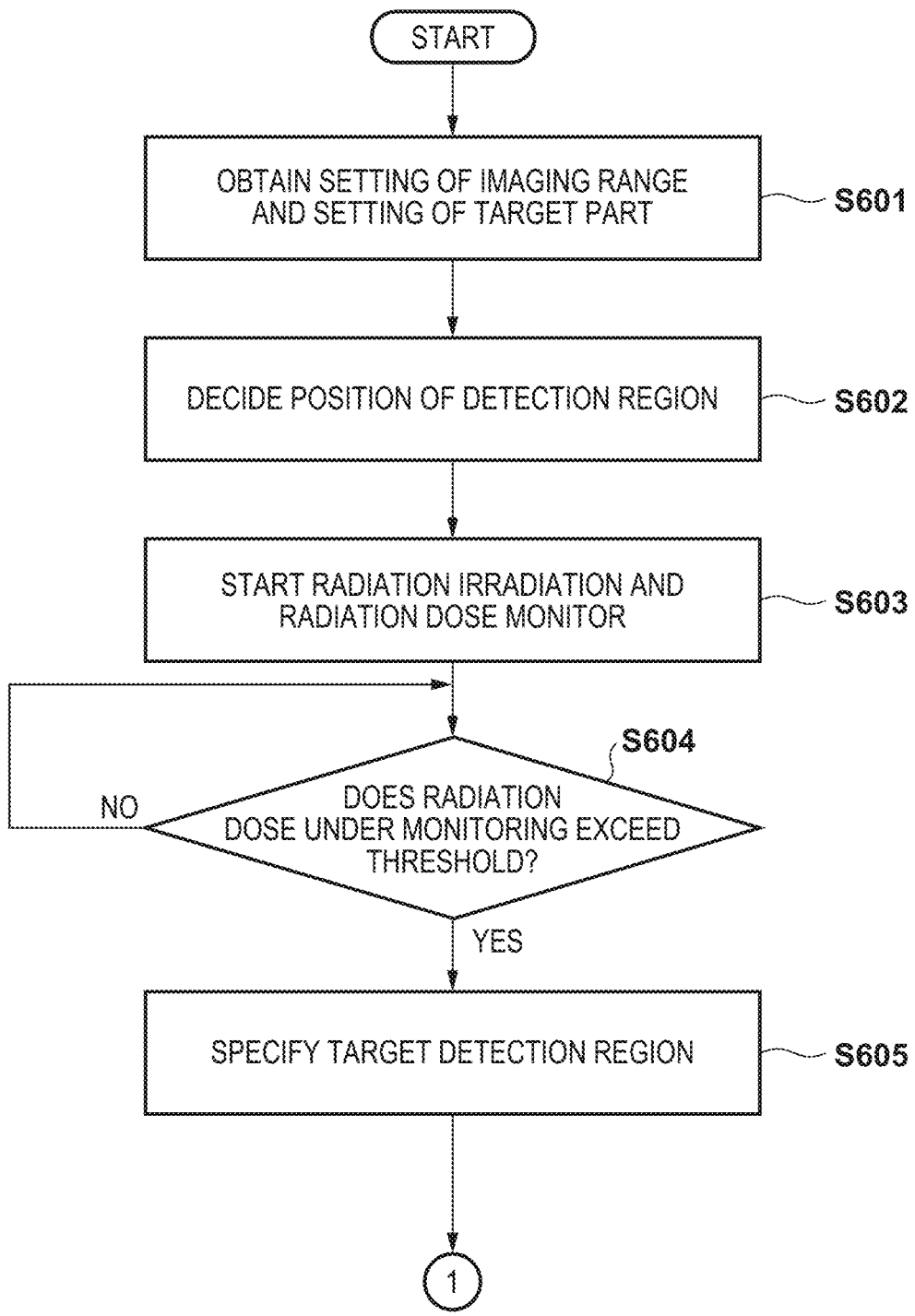
FIG. 6A is a flowchart for explaining an example of the operation of the radiation detection apparatus according to the embodiment of the present disclosure.
Figure 6B:
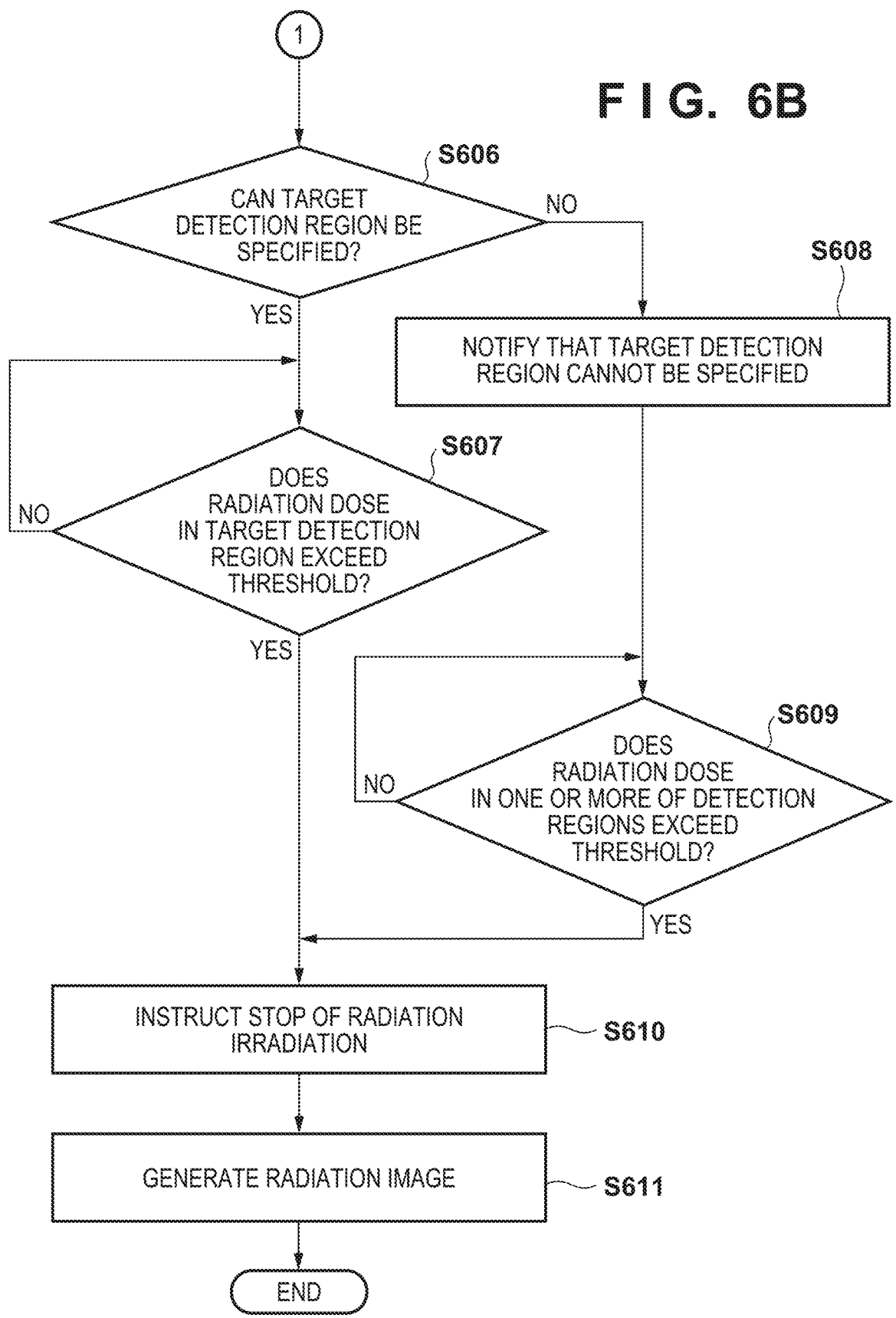
FIG. 6B is a flowchart for explaining an example of the operation of the radiation detection apparatus according to the embodiment of the present disclosure.

In the method shown in FIGS. 6A and 6B, after a target part is set in step S601, a detection region is decided in accordance with the target part in step S602. Instead, the user may designate a target part from a detection region set in advance. Detection regions to be set in advance may be five detection regions as shown in FIG. 3B, 3 rows×3 columns=9 detection regions, or 5 rows×5 columns=25 detection regions.

Processing to be performed by the control unit 140 using the method shown in FIGS. 6A and 6B may be executed by the control circuit 240 incorporated in the radiation detection apparatus 100 or another device (circuit).

The radiation dose monitored by the radiation detection apparatus 100 is affected by noise such as quantum noise included in radiation or system noise of the read circuit 220. The above-described thresholds Th1 to Th3 may be values larger than the noise level. For example, if a region where the radiation irradiation amount is small is a target part, system noise is dominant. Hence, the control circuit 240 may set the above-described thresholds Th1 to Th3 based on the system noise. If a region where the radiation irradiation amount is large is a target part, quantum noise is dominant. Hence, the control circuit 240 may set the above-described thresholds Th1 to Th3 based on the quantum noise. The noise level may be, for example, information associated with irradiation intensity or information associated with a sampling count, or may be linked with information that constitutes noise.

Figure 8:
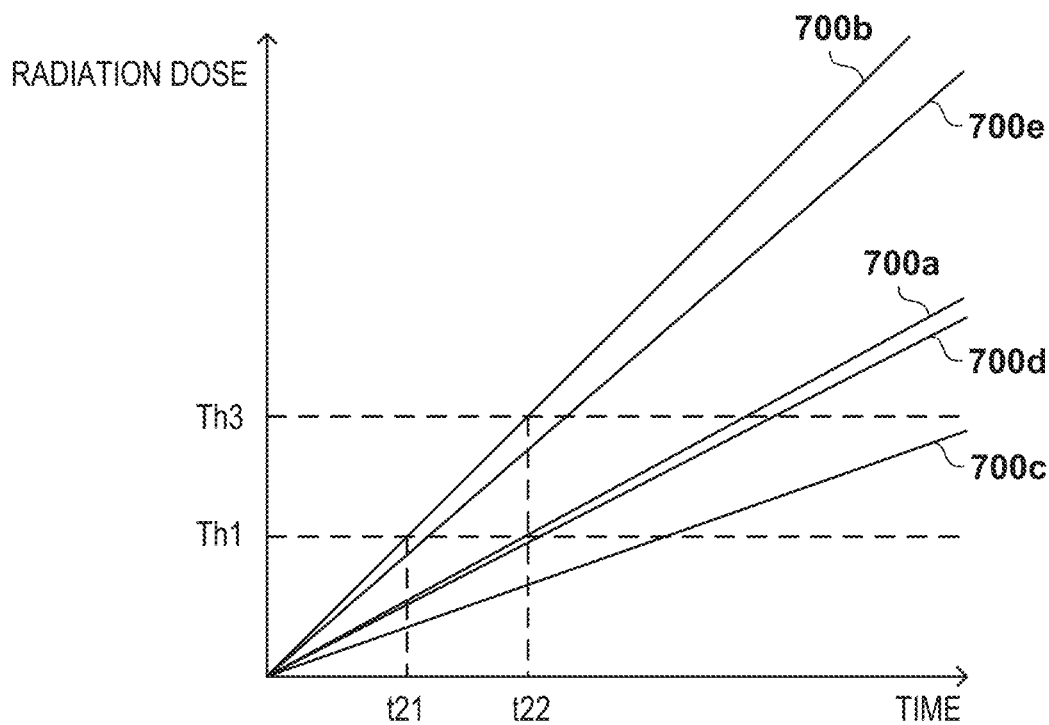
FIG. 8 is a view for explaining 2-step estimation of a target detection region according to the embodiment of the present disclosure.

In step S605, the control circuit 240 may perform estimation of at least one target detection region twice based on the radiation transmission amounts set for the plurality of parts and the radiation doses monitored in the plurality of detection regions. If the two estimation results match, the control circuit 240 may specify the estimation result as at least one target detection region. More specifically, as shown in FIG. 8, at time t21 when the radiation dose under monitoring exceeds the threshold Th1, the control circuit 240 estimates at least one target detection region as in step S605 described above. After that, at time t22 when the radiation dose under monitoring exceeds the threshold Th2, the control circuit 240 estimates at least one target detection region as in step S605 described above. If the at least one target detection region estimated at time t21 matches the at least one target detection region estimated at time t22, the control circuit 240 specifies the estimation result as at least one target detection region. If the results are different, the control circuit 240 may repeat the determination while increasing the threshold stepwise until continuously obtained estimation results match. By this estimation method, even if the noise level changes suddenly due to the influence of a magnetic field or a power supply noise, the target detection region can be specified without causing a recognition error. In addition, when specifying the target detection region, if it can be determined that the noise level suddenly changes, the region may be specified again after the noise output is excluded or corrected.

Figure 9:
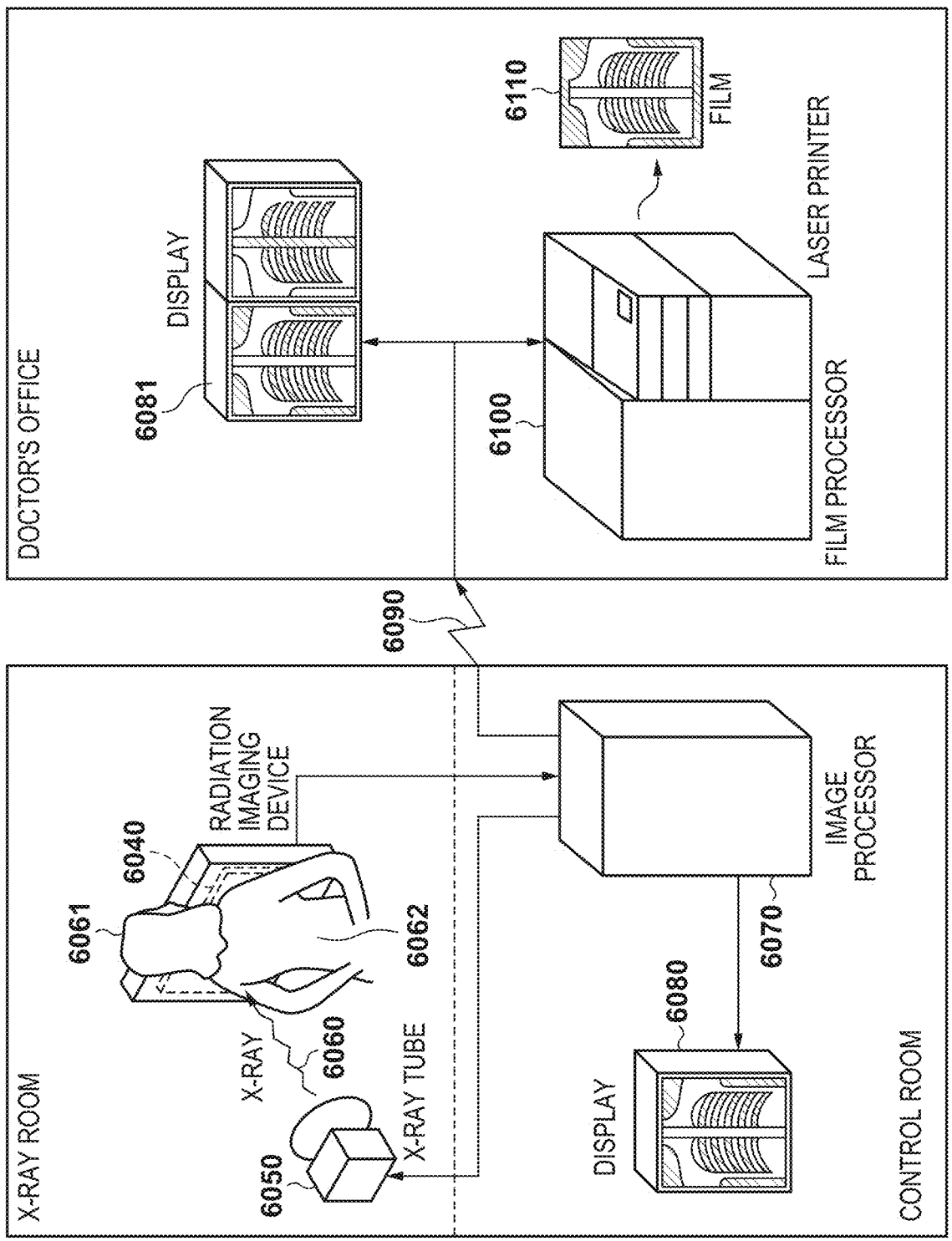
FIG. 9 is a view for explaining an example of the configuration of a radiation detection system according to the embodiment of the present disclosure.

FIG. 9 is a view showing an example of application of the above-described radiation detection apparatus to an X-ray diagnosis system (radiation detection system). X-rays 6060 generated as radiation by an X-ray tube 6050 (radiation source) pass through a chest 6062 of an object or patient 6061 and enter a radiation detection apparatus 6040. The radiation detection apparatus 6040 may be the above-described radiation detection apparatus 100. The incident X-rays include the internal body information of the patient 6061. A scintillator emits light in correspondence the incidence of the X-rays, and the light is photoelectrically converted to obtain electrical information. This information is converted into a digital signal, undergoes image processing by an image processor 6070 serving as a signal processing unit, and can be observed on a display 6080 serving as a display unit in a control room. Note that the radiation detection system includes at least a detection apparatus and a signal processing unit for processing a signal from the detection apparatus.

Also, this information can be transferred to a remote place by a transmission processing unit such as a telephone line 6090. This allows the information to be displayed on a display 6081 serving as a display unit in a doctor's office in another place or to be stored in a recording unit such as an optical disk, and allows a doctor in a remote place to make a diagnosis. In addition, a film processor 6100 serving as a recording unit can record the information on a film 6110 serving as a recording medium.

According to the embodiments described above, it is possible to accurately specify a detection region as a target of automatic exposure control.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation detection apparatus capable of monitoring a radiation dose during incidence, the apparatus comprising:
   an obtaining unit configured to obtain a setting of an imaging range including a plurality of parts of an object and a setting of at least one target part that is a target of automatic exposure control in the plurality of parts;
   a specifying unit configured to specify, based on radiation transmission amounts set for the plurality of parts and radiation doses monitored in a plurality of detection regions of the radiation detection apparatus, at least one target detection region, from the plurality of detection regions, located at a position where radiation transmitted through the at least one target part enters; and
   an output unit configured to output the radiation dose monitored in the at least one target detection region.

2. The radiation detection apparatus according to claim 1, wherein the specifying unit compares a distribution of the radiation transmission amounts set for the plurality of parts and a distribution of the radiation doses monitored in the plurality of detection regions, thereby specifying the at least one target detection region.

3. The radiation detection apparatus according to claim 1, further comprising a notification unit configured to, in a case where the specifying unit cannot specify the at least one target detection region, make a notification to a user of the radiation detection apparatus.

4. The radiation detection apparatus according to claim 1, wherein in a case where the specifying unit cannot specify the at least one target detection region, the output unit outputs a radiation dose monitored in one or more of the plurality of detection regions.

5. The radiation detection apparatus according to claim 1, wherein the specifying unit specifies the at least one target detection region after the radiation dose in at least one of the plurality of detection regions exceeds a threshold.

6. The radiation detection apparatus according to claim 1, wherein the specifying unit specifies the at least one target detection region after the radiation doses in all of the plurality of detection regions exceed a threshold.

7. The radiation detection apparatus according to claim 1 wherein the specifying unit performs estimation of the at least one target detection region twice based on the radiation transmission amounts set for the plurality of parts and the radiation doses monitored in the plurality of detection regions of the radiation detection apparatus, and in a case where the two estimation results match, specifies the estimation result as the at least one target detection region.

8. The radiation detection apparatus according to claim 1, wherein the plurality of detection regions are arranged in two-fold symmetry.

9. The radiation detection apparatus according to claim 1, wherein the plurality of detection regions are arranged in four-fold symmetry.

10. An output method of a radiation detection apparatus capable of monitoring a radiation dose during incidence, the method comprising:
- obtaining a setting of an imaging range including a plurality of parts of an object and a setting of at least one target part that is a target of automatic exposure control in the plurality of parts;
- specifying, based on radiation transmission amounts set for the plurality of parts and radiation doses monitored in a plurality of detection regions of the radiation detection apparatus, at least one target detection region, from the plurality of detection regions, located at a position where radiation transmitted through the at least one target part enters; and
- outputting the radiation dose monitored in the at least one target detection region.

\* \* \* \* \*